United States Patent [19]

Akiyama et al.

[11] Patent Number: 5,204,705
[45] Date of Patent: Apr. 20, 1993

[54] OPHTHALMIC MEASUREMENT APPARATUS

[75] Inventors: Koichi Akiyama, Choufu; Masunori Kawamura, Aichi, both of Japan

[73] Assignee: Kowa Company Ltd., Japan

[21] Appl. No.: 731,740

[22] Filed: Jul. 16, 1991

[30] Foreign Application Priority Data

Jul. 23, 1990 [JP] Japan .................................. 1-193046

[51] Int. Cl.⁵ .............................................. A61B 3/10
[52] U.S. Cl. .................................... 351/221; 351/214; 128/745
[58] Field of Search ............... 351/205, 211, 214, 221, 351/246; 128/633, 745; 606/4

[56] References Cited

U.S. PATENT DOCUMENTS 3,963,019 6/1976 Quandt .................................... 356/39
4,650,301 3/1987 Humphrey ........................... 351/211

FOREIGN PATENT DOCUMENTS 299710 1/1989 European Pat. Off. ............. 351/221

Primary Examiner—Rodney B. Bovernick
Attorney, Agent, or Firm—Bruce L. Adams; Van C. Wilks

[57] ABSTRACT

An ophthalmic measurement apparatus projects a laser beam into an eye and performs measurements using the light scattered by floating cells in the eye. The aperture area of the mask that defines the field of measurement view is adjusted to correspond to measurement conditions in the eye. A system processor determines the number of floating cells based on signals from a photosensor disposed behind the mask aperture and corrects the cell count according to a predetermined formula. The aperture area of the mask is changed depending on the counted number of floating cells in such a manner that the size of the mask aperture is decreased when there are many cells in the eye and increased when there are few cells in the eye.

9 Claims, 6 Drawing Sheets

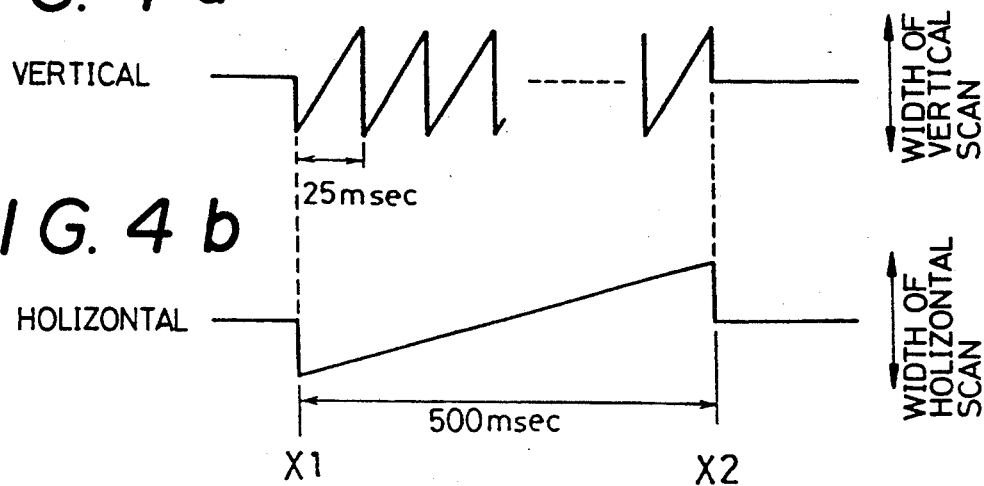
FIG. 4a
FIG. 4b
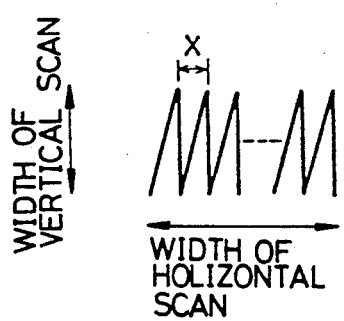
FIG. 5
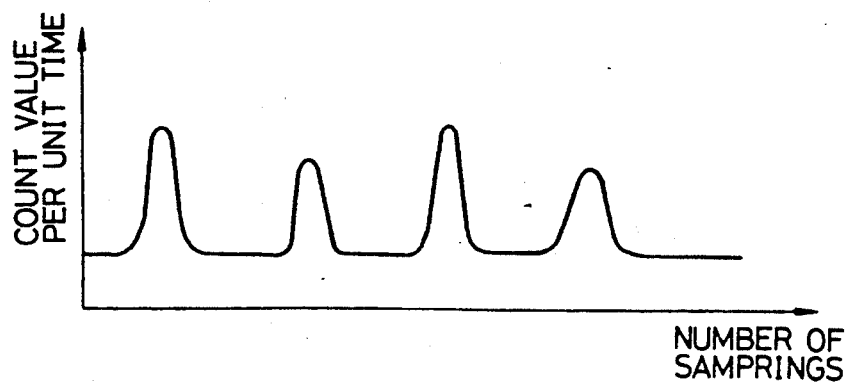
FIG. 6

OPHTHALMIC MEASUREMENT APPARATUS

BACKGROUND OF THE INVENTION

1. Field of the Invention

This invention relates to an ophthalmic measurement apparatus. More particularly, this invention relates to an ophthalmic measurement apparatus that irradiates the interior of a subject's eye with a beam of laser light and uses the light scattered from the interior of the eye to perform specific measurements.

2. Description of the Prior Art

Measurement of floating cells in the anterior chamber of the eye is of critical importance when diagnosing ophthalmic inflammations, especially malfunctions of the blood-aqueous barrier and uveitis. Conventionally a slit lamp microscope is often used for this, with grading being determined via the naked eye. On the other hand, a photographic measuring method has been developed to provide quantitative measurements. However, no method has yet been perfected that is readily applicable to clinical examinations.

An example of an ophthalmic measurement method in which the eye is irradiated with a beam of laser light and the light scattered from the eye is detected is disclosed in the Japanese Patent Publication No. Sho 64-2623 (corresponding to U.S. Pat. No. 5,000,562).

However, in such methods the size of the mask aperture is fixed and the concentration of floating cells in the anterior chamber (hereinafter referred to as "cells") may be such that two or more cells enter the laser beam at the same time. This can be a problem if two cells are counted as one because the indicated count will be lower than the actual count, degrading the measurement accuracy. Reducing the size of the mask aperture to prevent this also decreases the volume of the measurement portion, and in cases where the cell concentrations are low this results in an intermittent count that degrades reproducibility and produces inconsistent results.

This problem, will now be explained with reference to FIGS. 9a and 9b. FIG. 9a shows the measurement field of view in an eye as observed using a measurement system apparatus. In the drawing, L indicates a laser beam. Measurements by the system's photosensing section are performed laterally on the region illuminated by the laser beam. The measurement field of view is defined by the use of a specific aperture of a mask arranged in front of the system photosensor.

The presence of two cells (particles) C in the laser beam that are in line along the direction of beam propagation causes superimposition of the scattered light peaks, shown in FIG. 6, so the two cells are counted as one.

A possible solution is to reduce the size of the mask aperture, as shown in FIG. 9b. Although this arrangement decreases the probability of two cells being counted as one, it also decreases measurement volume which, when cell concentrations are low, degrades measurement reproducibility and, when visual observations are conducted results in inconsistent readings.

SUMMARY OF THE INVENTION

It is therefore an object of the present invention to provide an ophthalmic measurement apparatus whereby measurement conditions such as measurement volume can be adjusted to correspond to the degree of inflammation of the eye being examined, and cell counts can be accurately measured.

In accordance with the present invention, this object is attained by an ophthalmic measurement apparatus in which ophthalmic measurement is performed by projecting a laser beam into an eye and detecting light scattered by floating cells in the eye. The inventive apparatus comprises a laser beam projection section for converging a laser beam from a laser source to a predetermined point in the eye. A light receiving section is provided with a photosensor for detecting scattered laser light from within the eye. A mask defines a field of view and is arranged in front of the photosensor. Means are provided for adjusting the aperture area of the mask. Processing means are provided for performing ophthalmic measurements by processing signals from the photosensor. Means are provided for scanning the laser beam vertically and horizontally, and control means are provided for changing the size of the mask aperture to correspond to measurement conditions in the eye.

In a preferred embodiment of the invention in which signals from the photosensor are subjected to prescribed processing by the processing means to count floating cells, a method based on binomial distribution is used to establish the probability of a multiplicity of anterior-chamber floating cells being present within the region illuminated by the laser beam in the field of view defined by the mask, and the processing means is used output a corrected cell count.

BRIEF DESCRIPTION OF THE DRAWINGS

The objects and features of the present invention will become more apparent from a consideration of the following detailed description taken in conjunction with the accompanying drawings, in which:

FIGS. 4a and 4b are laser beam scanning signal waveforms;

FIG. 5 is an explanatory diagram showing the track of the scanning laser beam from the perspective of the laser beam aperture;

FIG. 6 is a curve showing peaks produced by light scattered by floating matter;

DETAILED DESCRIPTION OF THE PREFERRED EMBODIMENTS

Figure 1:
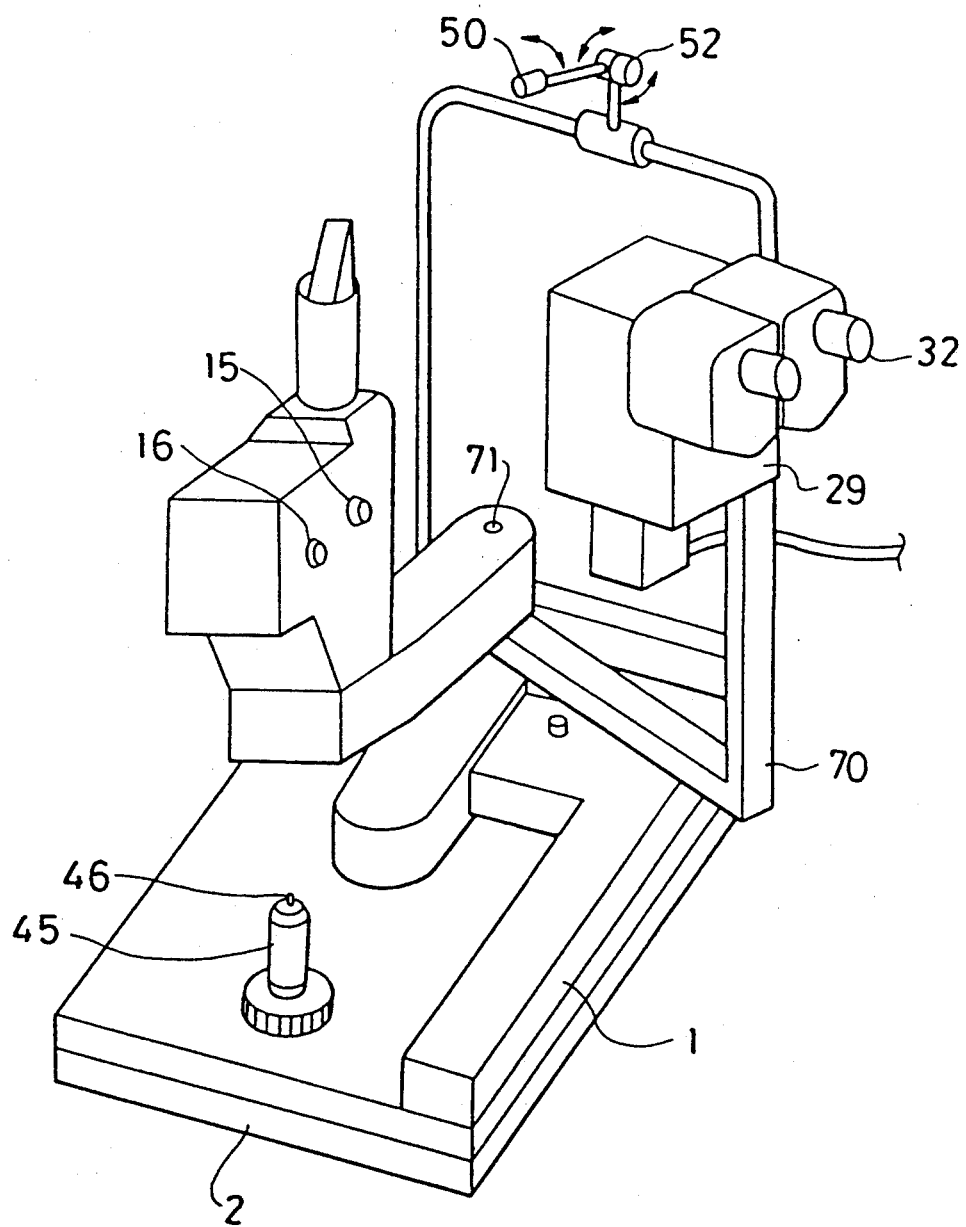
FIG. 1 is a perspective view of the apparatus according to the present invention.
Figure 2:
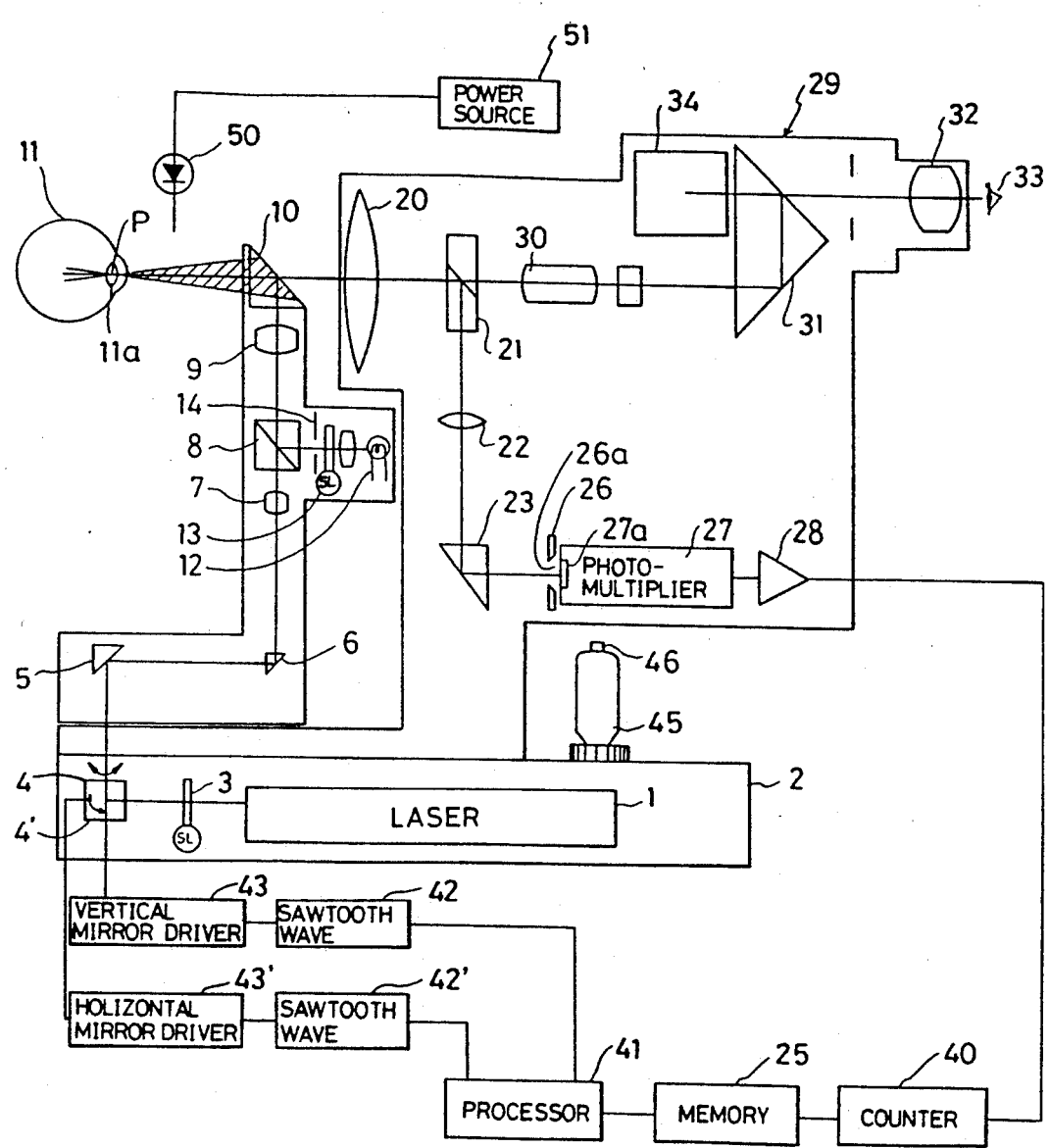
FIG. 2 is a diagram showing the arrangement of the optical system of the apparatus.
Figure 3:
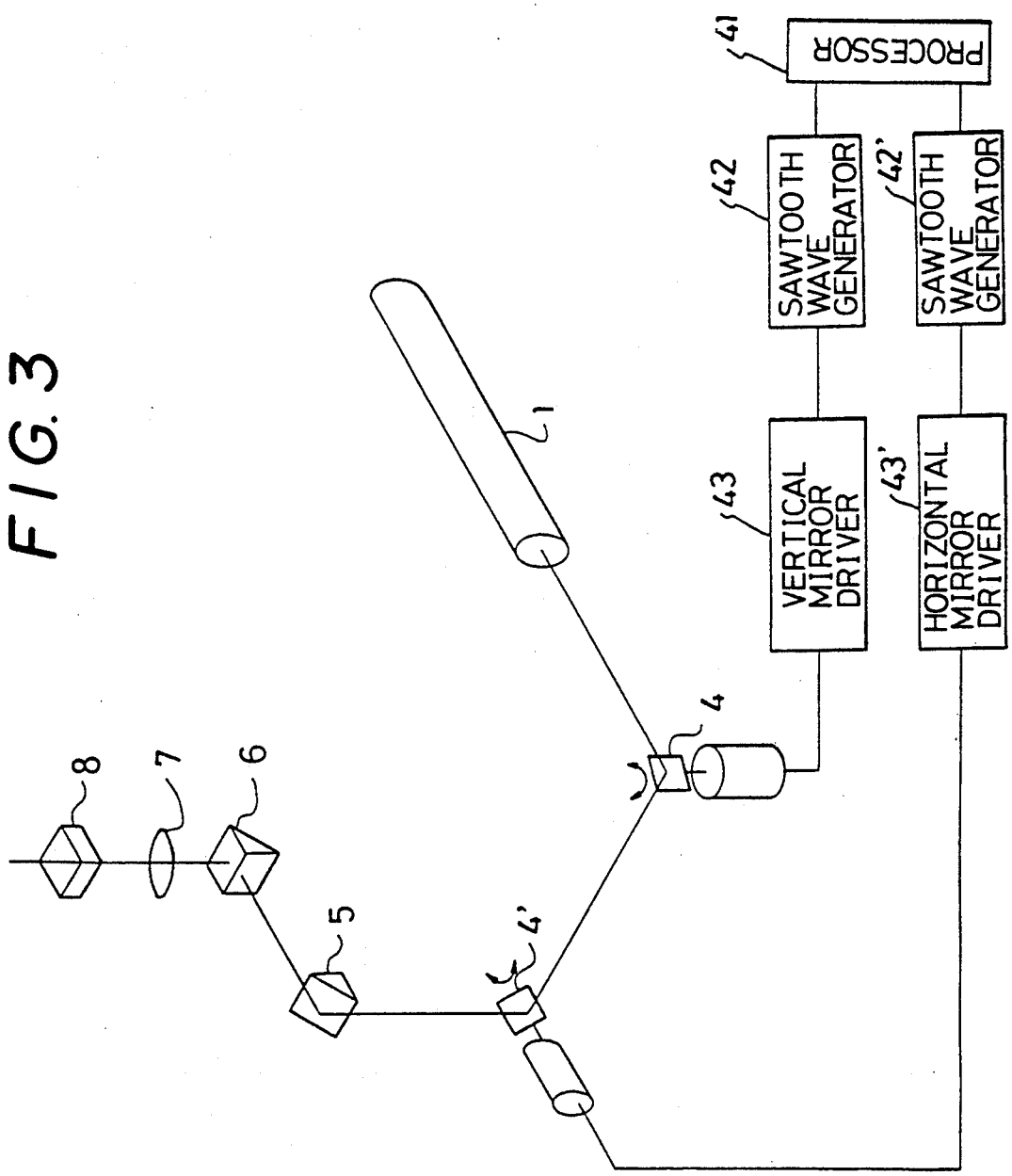
FIG. 3 is a diagram showing the arrangement of the optical system for scanning the laser beam.

The invention will now be described in detail with reference to the drawings. FIGS. 1 to 3 show an arrangement of the ophthalmic disease detection apparatus according to the present invention. Reference numeral 1 denotes a laser light source, such as, for example, a helium-neon or argon laser source. The laser light source 1 is disposed on a stand 2. Light from the laser light source 1 is passed through a laser beam filter 3 and through a vertical scanning mirror 4, a horizontal scanning mirror 4', prisms 5 and 6, a lens 7, a beam splitter 8, a condenser lens 9 and a prism 10 to converge on the eye under examination 11 at a spot in the anterior chamber 11a thereof.

The laser beam projector is provided with a slit light source 12. Light from the slit light source 12 passes through a slit light shutter 13 and a slit 14 and goes through the beam splitter 8, lens 9 and prism 10 to form a slit image on the anterior chamber 11a. With the light from the laser light source being converged to a spot, this slit image is for illuminating the surrounding area to facilitate confirmation of the position of the spot of converged light.

The width and length of the slit 14 can be adjusted by an adjusting knob 15 and a switching knob 16, respectively, which are shown in FIG. 1.

A portion of the laser light scattered from the measuring spot in the anterior chamber 11a passes through an objective lens 20 of a detection section 29 and is split by a beam splitter 21. One part of the light thus split passes through a lens 22, a prism 23 and a mask 26 provided with a slit 26a and impinges on a photomultiplier 27 that constitutes the photosensor. The other part of the scattered light split by the beam splitter 21 passes via a lens 30 and prisms 31 and 34 to an eyepiece 32 by means of which an examiner 33 can carry out observations.

The output from the photomultiplier 27 is passed through an amplifier 281 and is input to a counter 40 and the intensity of the scattered light detected by the photomultiplier is counted as numbers of pulses per unit time period. The output of the counter 40, i.e., the number of samplings or the total pulse count, is stored in a memory 25 allocated for each unit time period. The data stored in the memory 25 is processed by a processor 41 which, as explained below, computes a count of floating matter in the anterior chamber.

FIG. 3 shows details of the vertical and horizontal scanning mirrors 4 and 4'. Under the control of the processor 41, the mirrors are caused to swing vertically or horizontally by means of sawtooth wave generators 42 and 42' and vertical and horizontal scanning mirror drive circuits 43 and 43', causing the laser beam to scan vertically and horizontally. Thus, enabling the spot of laser light to be moved vertically and horizontally within the anterior chamber. The scanning of the spot of laser light is arranged so that the scan does not exceed the vertical dimension of the slit 26a, as measured from the center of the slit.

In accordance with this invention, an eye fixation light 50 constituted of a light-emitting diode or the like powered by electricity supplied from a power source 51 is disposed at a position that permits the examiner to fix the patient's eye. The light selected for the eye fixation light 50 is of a different color than the light of the laser light source 1. For example, when the light from the laser light source is red, a green light is selected. The eye fixation light 50 can be turned in the direction indicated by the arrow by means of a link mechanism 52 to enable it to be adjusted so that it is always in an optimum position with respect to the patient's eye.

Provided on the base 2 is an input means, such as a joystick 45 equipped with a push-button 46, and this can be operated to insert the laser filter 3 and the slit light shutter 13 into, or retract the said elements from, the respective optical system., The operation of the apparatus arranged in accordance with the present invention will now be described. In conducting the measurement, the slit light source 12 is activated and an image of the slit 14 is formed, via the beam splitters 8 and 10 and the lens 9, and the prism 10, on a part of the anterior chamber 11a that includes the measurement point P. Following this, light from the laser light source 1 is converged on the measuring point P via the optical system.

A portion of the light from the measuring point P is simultaneously directed by the beam splitter 21 to the examiner 33 for observation and through a lens 22, a prism 23 and the mask 26 to impinge on the photomultiplier 27.

Under the control of the processor 41, scanning is performed by the vertical and horizontal scanning mirrors 4 and 4' by means of sawtooth wave generators 42 and 42' and vertical and horizontal scanning mirror drive circuits 43 and 43'.

The sawtooth wave generators 42 and 42' each produce the type of signal shown in FIGS. 4a and 4b for the scanning of the laser beam. In the drawing X1 indicates the starting point of the measurement and X2 the completion of the measurement. If horizontal frequency is $H_f$ and vertical frequency is $V_f$ and the number of vertical scans is N, then $H_f = V_f/N$.

The vertical and horizontal scanning mirrors 4 and 4' are scanned in accordance with the signal waveforms, causing the laser beam to perform scanning with measurement point P at the center of the scan. FIG. 5 shows the actual scanning state as seen from the laser beam projector. In order to remove noise components formed by light reflections in the eye and efficiently receive signals derived from the scattered light, the width of the vertical scan is set smaller than the vertical width of the slit 26a.

Thus, the photomultiplier 27 receives the incident scattered laser light via the slit 26a, detects the intensity of the light that has been scattered by floating particles in the anterior chamber 11a and converts this into a corresponding series of pulses which are counted by a counter 40 as number of pulses per unit time period, and the count values are then stored in a memory 25 allocated for each unit time period.

Because the floating particles in the anterior chamber which are the object of the measurement are larger than several micrometers in diameter, when the laser beam passes across a floating particle the scattered-light intensity registers a peak. Therefore, if the measurement of floating particles is carried out with the measurement unit time period set so as to be shorter than the time required for the laser to traverse a floating particle, and the count data stored in the memory 25 is represented as a time-series, count values will only show an increase where the laser beam traverses a floating particle, thereby producing the kind of waveform illustrated in FIG. 6. In FIG. 6, each peak was produced by light scattered by a floating particle. Counting the peaks by means of the processor 41 enables measurement of the number of floating particles (cells) within the anterior chamber space that is scanned vertically and horizontally by the laser beam.

Moreover, if the laser beam is moving at a constant velocity when it traverses a floating particle and the diameter of the laser beam is known beforehand, the size of the particles can be calculated from the width of the peak. To prevent the same particle being counted twice, the scanning waveform is given the sawtooth configuration shown in FIG. 5 and the horizontal scanning width is set so that the peak gap x is larger than the diameter of the laser beam.

Figure 7A:
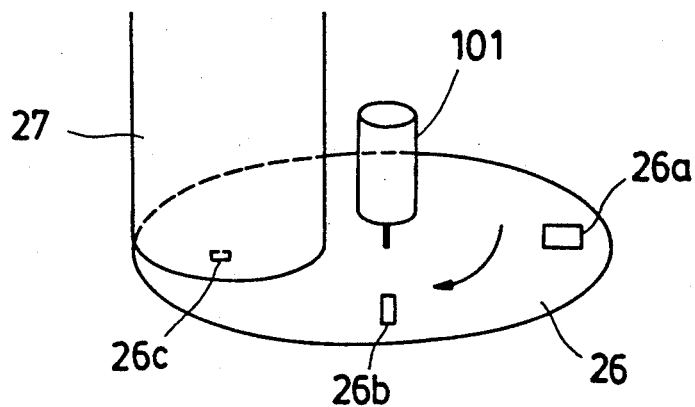
FIGS. 7a to 7c are explanatory diagrams of the mask aperture adjustment arrangement.
Figure 7B:
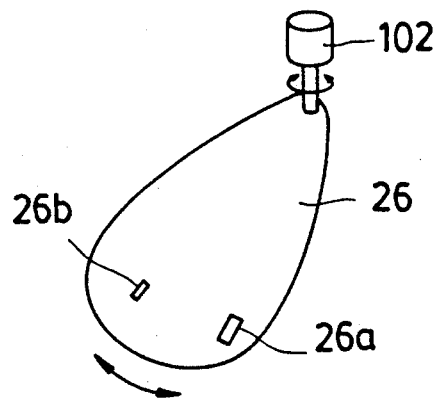
Figure 7C:
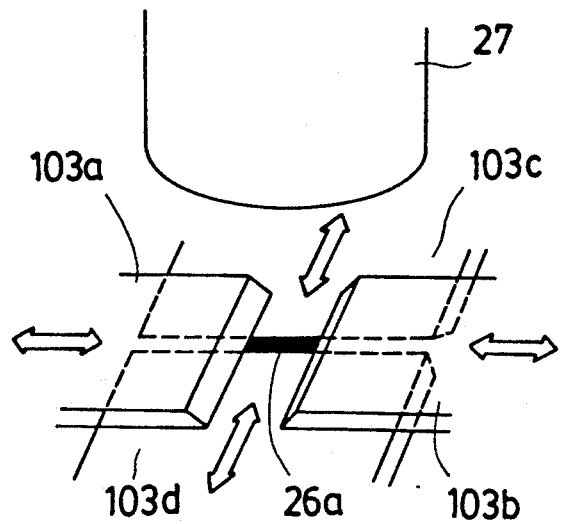

This invention employs a mechanism for changing the size of the slit 26a in the mask 26 so that it corresponds to the measurement conditions. FIGS. 7a to 7c show different embodiments of the mechanism for adjusting the mask aperture.

In the embodiment shown in FIG. 7a, the mask 26 is in the form of a disk provided with a multiplicity of slits 26a, 26b, 26c, (. . .,) of different sizes arranged equidistantly around the periphery of the disk. This disk-shaped mask 26 is rotated by a motor or other such drive means 101 to bring the slit of the required size into position in front of the light detecting face of the photomultiplier.

FIG. 7b shows a mask 26 with two slits 26a and 26b of different sizes. With this arrangement, the mask 26 only needs to be pivoted to select a slit, which can be done by using a solenoid or the like as the drive means 102.

FIG. 7c shows an arrangement that enables the slit area to be continuously varied. The slit area can be continuously varied by arranging knife-edge plates 103, 103b, 103c and 103d in front of the photomultiplier and using a motor or other drive means (not shown) to move the plates in the directions indicated by the arrows.

Thus, the above arrangements enable the size of the mask aperture to be adjusted, whereby more accurate cell counts can be achieved by decreasing the size of the aperture when there are many cells in the eye, and increasing the size of the aperture when there are few cells. Such an adjustment of the aperture size could perhaps be done by the examiner so that the size corresponds to the degree of ophthalmic inflammation. Another way would be to have the adjustment done automatically, based on the results of a preliminary measurement.

The measurement volume is determined by the mask aperture, so changing the aperture changes the measurement volume. Therefore, when the size of the mask aperture is changed, the count may be output as the number of cells per cubic millimeter, for example.

The method of correcting the cell count to compensate for count error will now be described. If there are N cells (particles) in a volume V, when there are n cells within an infinitely small volume $\Delta V$, the probability P(n) at that point is expressed (binomial distribution):

$$P(n) = N!/\{(n!(N-n)!\} \times (\Delta V/V)^n \times \{1-(\Delta V/V)\}^{N-n}$$

That is, the probability of there being two cells in $\Delta V$ is:

$$P(2) = N!/\{(2!(N-2)!\} \times (\Delta V/V)^2 \times \{1-(\Delta V/V)\}^{N-2}$$

Therefore, the probability of there being three cells in $\Delta V$ is:

$$P(3) = N!/\{(3!(N-3)!\} \times (\Delta V/V)^3 \times \{1-(\Delta V/V)\}^{N-3}$$

Figure 8:
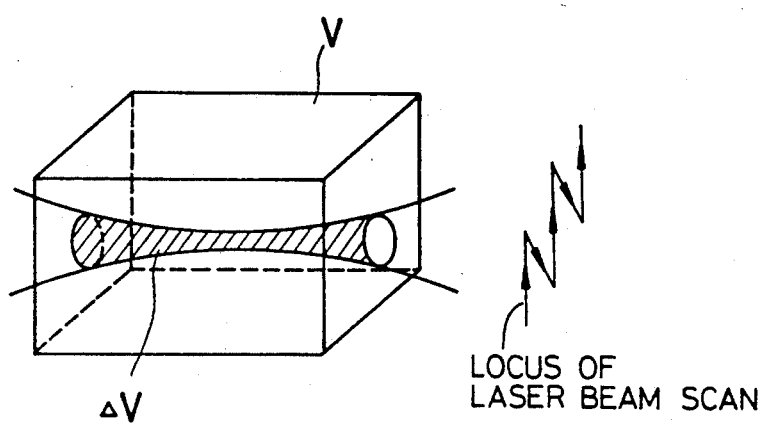
FIG. 8 is a diagram for explaining the ophthalmic measurement volume.
Figure 9A:
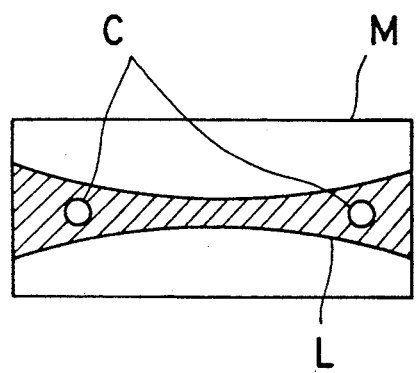
FIGS. 9a and 9b are diagrams for explaining the problems that arise when measuring floating cells.
Figure 9B:
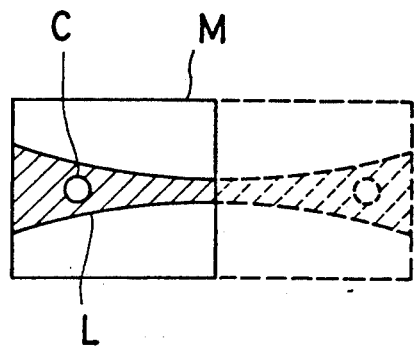

To apply this to the apparatus of this invention, if in the case of FIG. 8:
Volume of laser beam: $\Delta V$
Number of cells counted: N'
Actual number of cells in V: N
the average number (expected value) $\bar{n}$ of cells (particles) present in the laser beam is:

$$\bar{n} = 0\text{cells} \times P(0) = 1\text{cell} \times P(1) + \ldots = \sum_{K=0}^{N} \{k \times P(k)\}$$

which gives:

$$N = \bar{n} \times (V/\Delta V) = \sum_{K=0}^{N} \{k \times p(k)\} \times (V/\Delta V) \quad (1)$$

In fact, whether there are two cells or three cells in the beam they will in each case be counted as one, so at that point the average number (expected value) $\bar{n}'$ will be:

$$\begin{aligned}\bar{n}' &= 1\text{cell} \times P(1) + 1\text{cell} \times P(2) + \ldots \\ &= \sum_{K=1}^{N} \{1\text{cell} \times P(k)\} = 1\text{cell} \times \sum_{K=1}^{N} P(k) \\ &= 1\text{cell} \times \{1 - P(0)\} \left( \because \sum_{K=0}^{N} P(k) = 1 \right)\end{aligned}$$

therefore:

$$N' = \bar{n} \times (V/\Delta V) = \{1 - P(0)\} \times (V/\Delta V) \quad (2)$$

If $P(0) = \{1-(\Delta V/V)\}^N$ is substituted into equation (2) to resolve N, then:

$$N = \log(1-(\Delta V/V) \times N')/\log(1-(\Delta V/V)) \quad (3)$$

Correction is applied as follows. If $V=1$ mm$^3$, $\Delta V = 3.0 \times 10^{-4}$ mm$^3$, and N'=100 cells, then:

$$N = \log(1-(3.0 \times 10^{-4}/1) \times 100)-/\log(1-(3.0 \times 10^{-4}/1)) = 101.5$$

With the same conditions, if N'=1000 cells, N=1188.7 cells, meaning the count is about twenty percent on the low side.

Applying the above procedure to add a correction to the count value N' obtained by the photosensor enables a count N to be obtained that is near to the actual count value. For output, this corrected count N then only needs to be converted to a count value per cubic millimeter, as mentioned above.

It is to be understood as a matter of course that when the above-described means of adjusting the size of the mask aperture is used, the measurement volume value in each equation should be changed to correspond to size of the aperture being used.

In actual measurements, high cell concentrations can result in the simultaneous observation of scattered light from cell extremities and cell center portions, and a greater probability of cell superimposition in the depthhwise direction of observation. That is, the numbers of cells may cause unpredictable phenomena to occur. This can be handled by adding an unpredictability term to the above correction.

In the above (expected value) $\bar{n}'$, $$\bar{n}' = 1\text{ cell} \times P(1) + 1 \text{ cell} \times P(2) + 1 \text{ cell} \times P(3) + \ldots$$

This is made into:
$$\bar{n}' = 1 \text{ cell} \times P(1) \times f(1) + 1 \text{ cell} \times P(2) \times f(2) + 1 \text{ cell} \times P(3) \times f(3) + \ldots$$

Here, f(x){x=1,2,3, is taken as an unpredictability term that depends on the number of cells in the laser beam. Using $\bar{n}'$, N is obtained from $N' = n' \times (V/\Delta V)$.

With respect to f(x){x=1,2,3, ..., a more suitable value be obtained beforehand through experiments to obtain an N that is closer to N' (using the method of least squares or the like). The calculation takes time, but this method can be used when a more accurate value is required.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic measurement apparatus in which ophthalmic measurement is performed by projecting a laser beam into an eye and detecting light scattered by floating cells in the eye, comprising:
   a laser beam projection section for converging a laser beam from a laser source to a predetermined point in the eye;
   a light receiving section having a photosensor for detecting scattered laser light from within the eye and producing corresponding output signals;
   a mask for defining a field of view that is arranged in front of the photosensor;
   means for adjusting the aperture area of the mask;
   processing means for performing prescribed processing of signals from the photosensor for counting floating cells;
   means for scanning the laser beam horizontally and vertically; and
   control means for changing the size of the mask aperture depending on the counted number of floating cells in such a manner that the size of the mask aperture is decreased when there are relatively many cells in the eye and increased when there are relatively few cells in the eye.

2. An ophthalmic measurement apparatus according to claim 1; wherein the mask aperture adjustment means comprises a mask plate provided with a multiplicity of apertures and mounted to be rotated or swiveled.

3. An ophthalmic measurement apparatus according to claim 1; wherein the mask aperture adjustment means comprises knife-edges that are disposed vertically and horizontally and mounted so that each can be moved.

4. An ophthalmic measurement apparatus, comprising: projecting means for projecting a laser beam to irradiate a predetermined point in an eye; receiving means including a photosensor for receiving and detecting laser light scattered from the eye and producing corresponding output signals; a mask disposed in front of the photosensor and having an aperture for defining a field of view of the scattered laser light incident on the photodetector and defining a measurement volume; adjusting means for adjusting a size of the aperture of the mask; processing means receptive of signals from the photosensor for counting floating cells in the eye dependent on the scattered laser light; and control means receptive of signals from the processor for controlling the adjusting means to accordingly control adjustment of the size of the aperture depending on the counted number of floating cells such that the size of the aperture is decreased when relatively many floating cells are counted and the size of the aperture is increased when relatively few floating cells are counted.

5. An ophthalmic measurement apparatus according to claim 4; wherein the processing means for correcting a number N' of floating cells counted depending on a ratio of a volume $\Delta V$ of the laser beam incident at the predetermined point to the measurement volume V to obtain an actual number N of floating cells in the measurement volume V.

6. An ophthalmic measurement apparatus according to claim 5; wherein the means for correcting carries out correction according to a formula $N = \log(1-(\Delta V/V) \times N')/\log(1-(\Delta V/V))$ for correcting the number N'.

7. An ophthalmic measurement apparatus according to claim 4; further comprising means for scanning the laser beam horizontally and vertically.

8. An ophthalmic measurement apparatus according to claim 4; wherein the adjusting means comprises a mask plate having a plurality of differently sized apertures, each one of the apertures being selectively disposable in front of the photosensor.

9. An ophthalmic measurement apparatus according to claim 4; wherein the mask comprises movable knife-edges disposed vertically and horizontally; and the adjusting means includes means for moving the knife-edges to adjust the aperture of the mask.

* * * * *